(12) United States Patent
Hacker et al.

(10) Patent No.: US 6,677,276 B1
(45) Date of Patent: Jan. 13, 2004

(54) HERBICIDES FOR TOLERANT OR RESISTANT OIL SEED RAPE CULTURES

(75) Inventors: Erwin Hacker, Hochheim (DE); Hermann Bieringer, Eppstein (DE); Lothar Willms, Hofheim (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/762,673

(22) PCT Filed: Aug. 10, 1999

(86) PCT No.: PCT/EP99/05798

§ 371 (c)(1),
(2), (4) Date: Apr. 17, 2001

(87) PCT Pub. No.: WO00/08938

PCT Pub. Date: Feb. 24, 2000

(30) Foreign Application Priority Data

Aug. 13, 1998 (DE) .......................... 198 36 726

(51) Int. Cl.$^7$ .......................... A01N 33/18; A01N 43/42; A01N 43/56; A01N 47/36; A01N 57/04
(52) U.S. Cl. .......................... 504/127; 504/128; 504/130; 504/139
(58) Field of Search ................................ 504/127, 128, 504/130, 139

(56) References Cited

U.S. PATENT DOCUMENTS

| | | | |
|---|---|---|---|
| 5,739,082 A | 4/1998 | Donn ...................... | 504/206 |
| 6,239,072 B1 * | 5/2001 | Flint et al. .................. | 504/127 |

FOREIGN PATENT DOCUMENTS

| | | |
|---|---|---|
| WO | WO 97/36488 | 10/1997 |
| WO | WO 98/09525 | 3/1998 |

OTHER PUBLICATIONS

The Pesticide Manual, 10$^{th}$ Edition, Index 6, 1995, pp. 1335–1341, referred to as XP–002099499.
"Guidline on good plant protection practice. Beet.", Bull. OEPP (27, No. 2–3, 363–83, 1997), referred to as XP–002127724.
Weigl, W., "Winter Rape—Plant Protection Tips for Spring", Pflanzenarzt (45, No. 1–2, 12–13, 1992) 1 tab., Database accession No. 1992–81710 CROPU, referred to as XP–002125463.
Lichtner et al., "Ethametsulfuron methyl metabolism and crop selectively in spring oilseed rape (Brassica napus L.)", Pestic. Biochem. Physiol., (1995), 52(1), 12–24, Database accession No. 123–49745 CA, referred to as XP–002125461.
Kirkland et al., "Weed control in transgenic canola with glyphosate and registered canola herbicides", Res. Rep. Expert Comm. Weeds West. Can. (41 Meet., vol. 1, 242–43, 1994) 1 tab., Database accession No. 1995–86480 CROPU, referred to as XP–002125552.

* cited by examiner

*Primary Examiner*—S. Mark Clardy
(74) *Attorney, Agent, or Firm*—Frommer Lawrence & Haug LLP

(57) ABSTRACT

Suitable for controlling harmful plants in oil-seed rape composed of tolerant or resistant mutants or transgenic oil-seed rape plants, and, if appropriate, for regulating the growth of oil-seed rape, are herbicide combinations (A)+(B), if appropriate in the presence of safeners, with an effective content of (A) broad-spectrum herbicides from the group
  (A1) glufosinate (salts) and related compounds,
  (A2) glyphosate (salts) and related compounds such as sulfosate,
  (A3) imidazolinones such as imazethapyr, imazapyr, imazaquin, imazamox, imazapic or their salts and/or
  (A4) herbicidal azoles from the group of the inhibitors of protoporphyrinogen oxidase (PPO inhibitors), and
(B) herbicides from the group
  (B1) foliar- and soil-acting herbicides, such as metazachlor, trifluralin, clomazone, napropamide, carbetamide, dimefuron and dimethachlor, which are active against monocotyledonous and dicotyledonous harmful plants,
  (B2) predominantly foliar-acting herbicides, such as quinmerac, clopyralid, pyridate and ethametsulfuron-methyl, which are active against dicotyledonous harmful plants,
  (B3) predominantly foliar-acting herbicides, such as quizalofop-P and its esters, fenoxaprop-P and its esters, fluazifop-P and its esters, haloxyfop and haloxyfop-P and their esters and propaquizafop, which are active against monocotyledonous harmful plants, and/or
  (B4) foliar- and soil-acting herbicides, such as sethoxydim, cycloxydim and clethodim, which are active against monocotyledonous harmful plants.

25 Claims, No Drawings

HERBICIDES FOR TOLERANT OR RESISTANT OIL SEED RAPE CULTURES

This application is a 371 of PCT/EP99/05798 filed Aug. 10, 1999.

The invention relates to the field of the crop protection products which can be employed against harmful plants in tolerant or resistant crops of oil-seed rape and which comprise a combination of two or more herbicides as herbicidally active ingredients.

The introduction of tolerant or resistant oil-seed rape varieties and lines, in particular transgenic oil-seed rape varieties and lines, leads to the conventional weed control system being complemented by novel active ingredients which are nonselective per se in conventional oil-seed rape varieties. The active ingredients are, for example, the known broad-spectrum herbicides such as glyphosate, sulfosate, glufosinate, bilanafos (bialophos) and imidazolinone herbicides [herbicides (A)], which can now be employed in the tolerant crops developed for each of them. The efficacy level of these herbicides against harmful plants in tolerant crops is high, but, similarly as in the case of other herbicide treatments, depends on the nature of the herbicide employed, the application rate, the formulation in question, the harmful plants to be controlled in each case, the climatic and soil conditions and the like. Furthermore, the herbicides exhibit weaknesses (gaps) with regard to specific harmful plant species. Another criterion is the duration of action or the rate of degradation of the herbicide. Other factors which must be taken into account, if appropriate, are changes in the sensitivity of harmful plants, which may occur localized or upon prolonged use of the herbicides. Losses of action in individual plants can only be compensated for to some extent by increasing the application rates of the herbicides, if at all. Furthermore, there is always a need for methods for achieving the herbicidal action with a lower application rate of active ingredients. Not only does a lower application rate reduce the active ingredient quantity required for application, but, as a rule, it also reduces the quantity of formulation aids required. Both reduce the economic input and improve the ecological tolerance of the herbicide treatment.

A possibility of improving the use profile of a herbicide can be the combination of the active ingredient with one or more other active ingredients, which contribute the desired additional properties. However, phenomena of physical and biological incompatibility, for example lacking stability of a coformulation, decomposition of an active ingredient or antagonism of the active ingredients, occur not infrequently when using several active ingredients in combination. In contrast, what is desired is combinations of active ingredients with a favorable activity profile, high stability and the greatest degree of synergistically increased action, which allows reduction of the application rate compared with the individual application of the active ingredients to be combined.

Surprisingly, it has now been found that active ingredients from the group of the abovementioned broad-spectrum herbicide (A) in combination with other herbicides from group (A) and, if appropriate, certain herbicides (B) act synergistically in an especially advantageous manner when they are employed in the oil-seed rape crops which are suitable for the selective use of the first-mentioned herbicides.

Subject matter of the invention is thus the use of herbicide combinations for controlling harmful plants in oil-seed rape crops, wherein the herbicide combination in question comprises a synergistically effective content of (A) a broad-spectrum herbicide from the group of the compounds consisting of
(A1) compounds of the formula (A1)

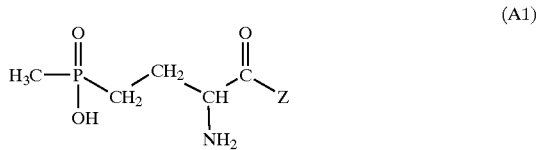

in which Z is a radical of the formula —OH or a peptide residue of the formula —NHCH(CH$_3$)CONHCH(CH$_3$)COOH or —NHCH(CH$_3$)CONHCH[CH$_2$CH(CH$_3$)$_2$]COOH, and its esters and salts, preferably glufosinate and its salts with acids and bases, in particular glufosinate-ammonium, L-glufosinate or its salts, bialaphos and its salts with acids and bases and other phosphinothricin derivatives, (A2) compounds of the formula (A2) and their esters and salts,

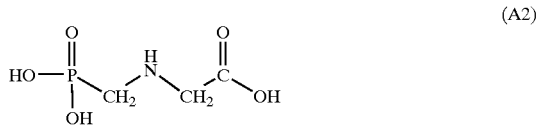

preferably glyphosate and its alkali metal salts or salts with amines, in particular glyphosate-isopropylammonium, and sulfosate, (A3) imidazolinones, preferably imazethapyr, imazapyr, imazamethabenz, imazamethabenzmethyl, imazaquin, imazamox, imazapic (AC 263,222) and their salts and (A4) herbicidal azoles from the group of the inhibitors of protoporphyrinogen oxidase (PPO inhibitors) such as WC9717 (=CGA276854), and (B) one or more herbicides from the group of the compounds consisting of
(B0) one or more structurally different herbicides from the abovementioned group (A) and/or
(B1) foliar- and soil-acting herbicides which are active against monocotyledonous and dicotyledonous harmful plants and/or
(B2) predominantly foliar-acting herbicides which are active against dicotyledonous harmful plants and/or
(B3) predominantly foliar-acting herbicides which are active in particular against monocotyledonous harmful plants and/or
(B4) foliar- and soil-acting herbicides which are active predominantly against monocotyledonous harmful plants, and the oil-seed rape crops tolerate the herbicides (A) and (B) present in the combination, if appropriate in the presence of safeners.

"Structurally different herbicides from the abovementioned group (A)" in group (B0) applies only to herbicides which are embraced by the definition of group (A) but which are not present as component (A) in the herbicide combination in question.

In addition to the herbicide combinations according to the invention, it is possible to use further crop protection agents and auxiliaries and formulation aids which are customary in crop protection.

The compounds are referred to by their common names and they are known from the "Pesticide Manual" 11th Ed., British Crop Protection Council 1997 (hereinbelow also abbreviated to "PM"). In addition to the herbicide combinations according to the invention, further crop protection active ingredients and formulation aids and auxiliaries conventionally used in crop protection may be used.

The synergistic effects are observed when the active ingredients (A) and (B) are applied jointly, but can also be observed upon split application (splitting). It is also possible to apply the herbicides or the herbicide combinations in several portions (sequential application), for example after pre-emergence uses, followed by post-emergence applications or after early post-emergence applications, followed by applications at the medium to late post-emergence stage. The simultaneous use of the active ingredients of the combination in question, if appropriate in several portions, is preferred. However, the split application of the individual active ingredients of a combination is also possible and may be advantageous in individual cases. Other crop protection agents such as fungicides, insecticides, acaricides and the like, and/or various auxiliaries, adjuvants and/or fertilizer applications can also be integrated into the use of this system.

The synergistic effects permit reduction of the application rates of the individual active ingredients, a more potent action against the same harmful plant species with the same application rate, the control of species to which the action has previously not extended (gaps), a widened application period and/or a reduced number of the individual applications required, and, as a result for the user, economically and ecologically more advantageous weed control systems.

For example, the combinations of (A)+(B) according to the invention make possible synergistically increased effects which far and unexpectedly exceed the effects which are achieved with the individual active ingredients (A) and (B).

WO-A-98/09525 has already been described a method of controlling weeds in transgenic crops which are resistant to phosphorus-containing herbicides such as glufosinate or glyphosate, where herbicide combinations are employed which comprise glufosinate or glyphosate and at least one herbicide from the group consisting of prosulfuron, primisulfuron, dicamba, pyridate, dimethenamid, metoachlor, flumeturon, propaquizafop, atrazin, clodinafop, norfurazone, ametryn, terbutylazine, simazine, prometryn, NOA-402989 (3-phenyl-4-hydroxy-6-chlorpyridazine), a compound of the formula

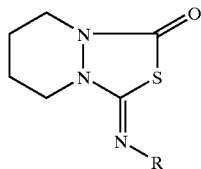

in which R=4-chloro-2-fluoro-5-(methoxycarbonylmethylthio)phenyl (disclosed in U.S. Pat. No. 4,671,819), CGA276854=1-allyloxycarbonyl-1-methylethyl 2-chloro-5-(3-methyl-2,6-dioxo-4-trifluoromethyl-3,6-dihydro-2H-pyrimidin-1-yl)benzoate (=WC9717, disclosed in U.S. Pat. No. 5,183,492) and 4-oxetanyl 2-{N-[N-(4,6-dimethylpyrimidin-2-yl)aminocarbonyl]aminosulfonyl}benzoate (disclosed in EP-A-496701). Details on the effects which can be or have been achieved cannot be found in the publication WO-A-98/09525. Examples of synergistic effects or on carrying out the method in particular crops are absent, as are specific combinations of two, three or further herbicides.

DE-A-2856260 discloses some herbicide combinations comprising glufosinate or L-glufosinate and other herbicides, such as alloxidim, linuron, MCPA, 2,4-D, dicamba, triclopyr, 2,4,5-T, MCPB and others.

WO-A-92/08353 and EP-A-0 252 237 disclose some herbicide combinations comprising glufosinate or glyphosate and other herbicides from the sulfonylurea group, such as metsulfuron-methyl, nicosulfuron, primisulfuron, rimsulfuron, inter alia.

In the publications, the use of the combinations for controlling harmful plants was demonstrated on only a few plant species, or else no examples were given.

It has been found in our own experiments that, surprisingly, large differences exist between the usability of the herbicide combinations mentioned in WO-A-98/09525 and the other references and also other novel herbicide combinations in plant crops.

In accordance with the invention, herbicide combinations are provided which can be employed particularly advantageously in tolerant oil-seed rape crops.

The compounds of the formulae (A1) to (A4) are known or can be prepared analogously to known methods.

Formula (A1) encompasses all stereoisomers and their mixtures, in particular the racemate and the biologically active enantiomer in each case, for example L-glufosinate and its salts. Examples of active ingredients of the formula (I) are the following:

(A1.1) glufosinate in the narrow sense, i.e. D,L-2-amino-4-[hydroxy-(methyl)phosphinyl]butanoic acid, (A1.2) glufosinate monoammonium salt, (A1.3) L-glufosinate, L- or (2S)-2-amino-4-[hydroxy(methyl)-phosphinyl]butanoic acid (=phosphinothricin), (A1.4) L-glufosinate monoammonium salt, (A1.5) bialaphos (or bilanofos), i.e. L-2-amino-4-[hydroxy(methyl)-phosphinyl] butanoyl-L-alanyl-L-alanine, in particular its sodium salt.

The abovementioned herbicides (A1.1) to (A1.5) are taken up via the green parts of the plants and are known as broad-spectrum herbicides or nonselective herbicides; they are inhibitors of the enzyme glutamine synthetase in plants; see "The Pesticide Manual" 11th Edition, British Crop Protection Council 1997, pp. 643–645 and 120–121. While there exists a field of application post-emergence for controlling broad-leaved weeds and grass weeds in plantation crops and on non-crop areas and, using specific application techniques, also for inter-row control in agricultural row crops such as maize, cotton and the like, the importance of the use as selective herbicides in resistant transgenic crops is increasing. Glufosinate is usually employed in the form of salt, preferably of the ammonium salt. The racemate of glufosinate or glufosinate-ammonium alone is usually applied at rates between 200 and 2000 g of A.S./ha (=g of a.i./ha=grams of active substance per hectare). At these rates, glufosinate is effective mainly when taken up via the green parts of the plants. However, since it is degraded microbially in the soil within a few days, it has no long-term action in the soil. This also applies analogously to the related active ingredient bialafos-sodium (also bilanafos-sodium); see "The Pesticide Manual" 11th Ed., British Crop Protection Council 1997, pp. 120–121. As a rule, markedly less active ingredient (A1) is required in the combinations according to the invention, for example an application rate in the range of 20 to 800, preferably 20 to 600, grams of active substance glufosinate per hectare (g of A.S./ha or g of a.i./ha). Corresponding quantities, preferably quantities converted into moles per hectare, also apply to glufosinate-ammonium and bilanafos, or bilanafos-sodium.

The combinations with the herbicides (A1) which are foliar-acting are expediently employed in oil-seed rape crops which are resistant to, or tolerate, the compounds (A1). Some tolerant oil-seed rape crops which have been produced by recombinant technology are already known and are employed in practice; cf. the article in the journal "Zuckerrübe", Vol. 47 (1998), p. 217 et seq.; for the production of transgenic plants which are resistant to glufosinate, cf. EP-A-0242246, EP-A-242236, EP-A-257542, EP-A-275957, EP-A-0513054.

Examples of compound (A2) are (A2.1) glyphosate, i.e. N-(phosphonomethyl)glycine, (A2.2) the monoisopropylammonium salt of glyphosate, (A2.3) the sodium salt of glyphosate, (A2.4) sulfosate, i.e. the trimesium salt of N-(phosphonomethyl)-glycine=the trimethylsulfoxonium salt of N-(phosphonomethyl)glycine.

Glyphosate is usually employed in the form of a salt, preferably of the monoisopropylammonium salt or the trimethylsulfoxonium salt (=the trimesium salt=sulfosate). Based on the free acid glyphosate, the individual dose is usually in the range of 0.5–5 kg of A.S./ha. Glyphosate resembles glufosinate with regard to some application aspects, but is, in contrast to the latter, an inhibitor of the enzyme 5-enolpyruvylshikimate-3-phosphate synthase in plants; see "The Pesticide Manual" 11$^{th}$ Ed., British Crop Protection Council 1997, pp. 646–649. As a rule, application rates in the range of 20 to 2000, preferably 20 to 1000, in particular 20 to 800, g of A.S./ha glyphosate are required in the combinations according to the invention.

In the case of compounds (A2), too, tolerant plants have been generated by recombinant methods and have been introduced into practice; cf. "Zuckerrübe", year 47 (1998), p. 217 et seq.; cf. also WO 92/00377, EP-A-115673, EP-A-409815.

Examples of imidazolinone herbicide (A3) are (A3.1) imazapyr and its salts and esters, (A3.2) imazethapyr and its salts and esters, (A3.3) imazamethabenz and its salts and esters, (A3.4) imazamethabenz methyl, (A3.5) imazamox and its salts and esters, (A3.6) imazaquin and its salts and esters, for example the ammonium salt, (A3.7) imazapic (AC 263,222) and its salts and esters, for example the ammonium salt.

The herbicides inhibit the enzyme acetolactate synthase (ALS) and thus protein synthesis in plants; they are both soil- and foliar-acting and some of them exhibit selectivities in crops; cf. "The Pesticide Manual" 11$^{th}$ Ed., British Crop Protection Council 1997 pp. 697–699 for (A3.1), pp. 701–703 for (A3.2), pp. 694–696 for (A3.3) and (A3.4), pp. 696–697 for (A3.5), pp. 699–701 for (A3.6) and pp. 5 and 6, reviewed under AC 263,222 (for A3.7). The application rates of the herbicides are usually between 0.001 and 2 kg of A.S./ha, in most cases from 0.1 to 2 kg of A.S./ha; specifically (A3.1) 20–400 g of A.S./ha, preferably 40–360 g of A.S./ha, (A3.2) 10–200 g of A.S./ha, preferably 20–180 g of A.S./ha, (A3.3) 100–2000 g of A.S./ha, preferably 150–1800 g of A.S./ha, (A3.4) 100–2000 g of A.S./ha, preferably 150–1800 g of A.S./ha, (A3.5) 1–150 g of A.S./ha, preferably 2–120 g of A.S./ha, (A3.6) 10–900 g of A.S./ha, preferably 20–800 g of A.S./ha, (A3.7) 5–2000 g of A.S./ha, preferably 10–1000 g of A.S./ha, In the combinations according to the invention, they are preferably in the range from 1 to 2000, in particular from 10 to 200, g of A.S./ha.

The combinations with imidazolinones are expediently employed in oil-seed rape crops which are resistant to the imidazolinones. Such tolerant crops are already known. For example, EP-A-0360750 describes the generation of ALS-inhibitor-tolerant plants by selection methods or by recombinant methods. The herbicide tolerance of the plants is generated here by an elevated ALS content in the plants. U.S. Pat. No. 5,198,599 describes sulfonylurea- and imidazolinone-tolerant plants which have been obtained by selection methods.

Examples of PPO inhibitors (A4) are (A4.1) pyraflufen and its esters, such as pyraflufen-ethyl, (A4.2) carfentrazone and its esters, such as carfentrazone-ethyl, (A4.3) oxadiargyl, (A4.4) sulfentrazone, (A4.5) WC9717 or CGA276854=1-allyloxycarbonyl-1-methylethyl 2-chloro-5-(3-methyl-2,6-dioxo-4-trifluoromethyl-3,6-dihydro-2H-pyrimidin-1-yl) benzoate (known from U.S. Pat. No. 5,183,492)

The abovementioned azoles are known as inhibitors of the enzyme protoporphyrinogen oxidase (PPO) in plants; see "The Pesticide Manual" 11th ed., British Crop Protection Council 1997, pp. 1048–1049 for (A4.1), pp. 191–193 for (A4.2), pp. 904–905 for (A4.3) and pp. 1126–1127 for (A4.4). The application rates of the azoles are generally in the range from 1 to 2000 g of A.S./ha, preferably from 2 to 1500 g of A.S./ha, in particular from 5 to 200 g of A.S./ha, specifically the following application rates of the individual active compounds:

(A4.1) from 1 to 100, preferably from 2 to 80, g of A.S./ha, (A4.2) from 1 to 500, preferably from 2–250, in particular 3–180, g of A.S./ha, (A4.3) from 10 to 1000, preferably 10–600, in particular 20–400, g of A.S./ha, (A4.4) from 10 to 2000, preferably 50–1500, preferably 70–1000, g of A.S./ha, (A4.5) from 10 to 1000 g of A.S./ha, preferably 20–800 g of A.S./ha.

Some plant crops which are tolerant to PPO inhibitors are already known.

Suitable combination partners (B) for component (A) are, for example, compounds of subgroups (B0) to (B4):

(B0) herbicides which differ structurally from (which are not identical with) herbicide (A), selected from the group of the herbicides which are possible for component (A), (B1) Herbicides which have both foliar and soil action and can be used against grasses and dicotyledonous plants, for example the following compounds (referred to by the common names and the reference in "The Pesticide Manual" 11th Ed., British Crop Protection Council 1997, abbreviated to "PM"; hereinbelow, preferred application rates are indicated in brackets):

(B1.1) metazachlor (PM, pp. 801–803), i.e. 2-chloro-N-(2,6-dimethylphenyl)-N-(1H-pyrazol-1-ylmethyl)

acetanilide, (100–3000 g of A.S./ha, in particular 200–3500 g of A.S./ha), (B1.2) trifluralin (PM, pp. 1248–1250), i.e. 2,6-dinitro-N,N-dipropyl4-trifluoromethylaniline, (200–5000 g of A.S./ha, in particular 500–3000 g of A.S./ha), (B1.3) clomazone (PM, pp. 256–257), i.e. 2-(2-chlorobenzyl)-4,4-dimethyl-1,2-isoxazolidin-3-one, (100–1000 g of A.S./ha, in particular 20–800 g of A.S./ha), (B1.4) napropamide (PM, pp. 866–868), i.e. (R,S)-N,N-diethyl-2-(1-naphthyloxy)propanamide, (200–3000 g of A.S./ha, in particular 300–2500 g of A.S./ha), (B1.5) carbetamide (PM, pp. 184–185), i.e. 1-(ethylcarbamoyl)ethyl (R)-carbanilic acid, (500–5000 g of A.S./ha, in particular 800–4000 g of A.S./ha) and (B1.6) dimefuron (PM, pp. 403404), i.e. 3-[4-(5-tert-butyl-2,3-dihydro-2-oxo-1,3,4-oxadiazol-3-yl)-3-chlorophenyl]-N,N-dimethylurea; (200–4000 g of A.S./ha, in particular 300–3000 g of A.S./ha) and optionally (B1.7) dimethachlor (PM, pp. 406407), 2-chloro-N-(2,6-dimethylphenyl)-N-(2-methoxyethyl)aceto-2',6'-xylilide, (30–4000 g of A.S./ha, in particular 200–3000 g of A.S./ha);

(B2) Herbicides which are predominantly foliar-acting and which can be employed against dicotyledonous plants, for example the compounds (B2.1) quinmerac (PM, pp.1080–1082), i.e. 7-chloro-3-methylquinoline-8-carboxylic acid and its salts, (50–1000 g of A.S./ha, in particular 80–800 g of A.S./ha), (B2.2) clopyralid (PM, pp. 260–263), i.e. 3,6-dichloropyridine-2-carboxylic acid and its salts, (20–1000 g of A.S./ha, in particular 30–800 g of A.S./ha), (B2.3) pyridate (PM, pp.1064–1066), i.e. O-(6-chloro-3-phenylpyridazin-4-yl) S-octyl thiocarbonate, (100–5000 g of A.S./ha, in particular 200–3000 g of A.S./ha);

(B2.4) ethametsulfuron-methyl (PM, pp. 475–476), i.e. methyl 2-{N-[N-(4-ethyox-6-methylamino-1,3,5-triazin-2-yl)aminocarbonyl]aminosulfonyl}benzoate; (1–500 g of A.S./ha, in particular 2–300 g of A.S./ha), (B3) herbicides which are predominantly foliar-acting and which can be employed against monocotyledonous harmful plants, for example the compounds:

(B3.1) quizalofop-P and its esters such as the ethyl or tefuryl ester (PM, pp.1089–1092), i.e. (R)-2-[4-(6-chloroquinoxalin-2-yloxy)phenoxy]propionic acid or its ethyl ester or tetrahydrofurfuryl ester, (10–300 g of A.S./ha, in particular 20–250 g of A.S./ha), also in the form of the mixtures with the S-isomer, e.g. as racemic quizalofop or its ester, (B3.2) fenoxaprop-P and its esters such as the ethyl ester (PM, pp. 519 to 520), i.e. (R)-2-[4-(6-chlorobenzoxazol-2-yloxy)phenoxy]propionic acid and its ethyl ester, (10–300 g/ha, in particular 20–250 g/ha), also in the form of the mixtures with the S-isomer, e.g. as racemic fenoxaprop or fenoxaprop-ethyl, (B3.3) fluazifop-P and its esters, such as the butyl ester (PM, pp. 556–557), i.e. (R)-2-[4-(5-trifluoromethylpyridyl-2-yloxy)-phenoxy]propionic acid and its butyl ester; (20–1500 g of A.S./ha, in particular 30 to 1200 g of A.S./ha), also in the form of the mixtures with the S-isomer, e.g. as racemic fluazifop or its ester, (B3.4) haloxyfop and haloxyfop-P and their esters such as the methyl or the etotyl ester (PM, pp. 660–663), i.e. (R,S)- and (R)-2-[4-(3-chloro-5-trifluoromethylpyrid-2-yloxy)phenoxy]-propionic acid and its methyl ester and etotyl ester, respectively, (10–300 g of A.S./ha, in particular 20–250 g of A.S./ha) and (B3.5) propaquizafop (PM, pp.1021–1022), i.e. isopropylideneaminooxyethyl (R)-2-[4-(6-chloroquinoxalin-2-yloxy)phenoxy]propionate, (10–300 g/ha, in particular 20–250 g/ha) and (B4) herbicides which are both foliar-acting and soil-acting and which can be employed against monocotyledonous harmful plants, for example (B4.1) sethoxydim (PM, pp.1101–1103), i.e. (E,Z)-2-(1-ethoxyiminobutyl)-5-[2-(ethylthio)propyl]-3-hydroxycyclohex-2-enone, (50–3000, in particular 100–200, g of A.S./ha), (B4.2) cycloxydim (PM, pp. 290–291), i.e. 2-(1-ethoxyiminobutyl)-3-hydroxy-5-thian-3-ylcyclohex-2-enone, (10–1000 g of A.S./ha, in particular 30–800 g of A.S./ha), (B4.3) clethodim (PM, pp. 250–251), i.e. 2-{(E)1-[(E)-3-chlorallyloxyimino]propyl}-5-[-2(ethylthio)propyl]-3-hydroxycyclohex-2-enone (10–800, in particular 20–600 g of A.S./ha).

The application rates of the herbicides (B) may vary greatly between the individual herbicides. The following ranges are rough indications:

Compounds (B0): 1–2000, preferably 5–2000, g of A.S./ha (cf. the information on the group of the compounds (A)

Compounds (B1): 10–5000 g of A.S./ha, in particular 20–4000 g of A.S./ha,

Compounds (B2): 1–5000 g of A.S./ha, in particular 2–3000 g of A.S./ha, very particularly preferably 10–2000 g of A.S./ha, Compounds (B3): 5–1500 g of A.S./ha, in particular 5–1200 g of A.S./ha, very particularly preferably 20–500 g of A.S./ha, Compounds (B4): 5–3000 g of A.S./ha, in particular 5–2000 g of A.S./ha, very particularly preferably 20–1000 g of A.S./ha, The quantitative ratios of the compounds (A) and (B) can be seen from the abovementioned application rates of the individual substances. For example, the following quantitative ratios are of particular interest:

(A):(B) in the range from 2000:1 to 1:5000, preferably from 750:1 to 1:1500, in particular from 400:1 to 1:1000, very particularly preferably from 200:1 to 1:400, (A):(B0) from 1000:1 to 1:400, preferably from 400:1 to 1:400, in particular from 200:1 to 1:200, very particularly preferably from 200:1 to 1:75, (A1):(B1) from 100:1 to 1:250, preferably from 50:1 to 1:200, in particular from 50:1 to 1:50, (A1):(B2) from 1000:1 to 1:250, preferably from 500:1 to 1:150, in particular from 100:1 to 1:50, very particularly preferably from 50:1 to 1:20, (A1):(B3) from 400:1 to 1:100, preferably from 100:1 to 1:100, in particular from 50:1 to 1:50, very particularly preferably from 20:1 to 1:5, (A1):(B4) from 200:1 to 1:200, preferably from 100:1 to 1:150, in particular from 100:1 to 1:100, very particularly preferably from 50:1 to 1:50, (A2):(B1) from 200:1 to 1:250, preferably from 100:1 to 1:200, in particular from 60:1 to 1:100, (A2):(B2) from 2000:1 to 1:250, preferably from 1000:1 to 1:150, in particular from 200:1 to 1:50, very particularly preferably from 60:1 to 1:20, (A2):(B3) from 500:1 to 1:100, preferably from 200:1 to 1:80, in particular from 100:1 to 1:60, very particularly preferably from 50:1 to 1:5, (A2):(B4) from 300:1 to 1:150, preferably from 200:1 to 1:150, in particular from 100:1 to 1:100, very particularly preferably from 50:1 to 1:50, (A3):(B1) from 200:1 to 1:5000, preferably from 100:1 to 1:4000, in particular from 50:1 to 1:1000, very particularly preferably from 20:1 to 1:500, most preferably from 10:1 to 1:100, (A3):(B2) from 2000:1 to 1:5000, preferably from 1000:1 to 1:3000, in particular from 500:1 to 1:1000, very particularly preferably from 20:1 to 1:500, most preferably from 10:1 to 1:100, (A3):(B3) from 200:1 to 1:1500, preferably from 100:1 to 1:1200, in particular from 50:1 to 1:600, very particularly preferably from 20:1 to 1:200, most preferably from 5:1 to 1:20, (A3):(B4) from 200:1 to 1:3000, preferably from 100:1 to 1:2000, in particular from 50:1 to 1:1000, very particularly preferably from 20:1 to 1:100, most preferably from 10:1 to 1:50, (A4):(B1) from 150:1 to 1:2500, preferably from 80:1 to 1:2000, in particular from 20:1 to 1:1000, very particularly preferably from 10:1 to 1:500, (A4):(B2) from 1500:1 to 1:2500, preferably from 750:1 to 1:1500, in particular from 20:1 to 1:1000, very particularly preferably from 10:1 to 1:500, (A4):(B3) from 150:1 to 1:100, preferably from 100:1 to 1:100, in particular from 75:1 to 1:60, very particularly preferably from 50:1 to 1:50, most preferably from 20:1 to 1:20

(A4):(B4) from 150:1 to 1:1500, preferably from 100:1 to 1:1000, in particular from 20:1 to 1:200, very particularly preferably from 10:1 to 1:100, The use of the following combinations is of particular interest:

(A1.1)+(B1.1), (A1.1)+(B1.2), (A1.1)+(B1.3), (A1.1)+(B1.4), (A1.1)+(B1.5), (A1.1)+(B1.6), (A1.1)+(B1.7), (A1.2)+(B1.1), (A1.2)+(B1.2), (A1.2)+(B1.3), (A1.2)+(B1.4), (A1.2)+(B1.5), (A1.2)+(B1.6), (A1.1)+(B1.7), (A1.1)+(B2.1), (A1.1)+(B2.2), (A1.1)+(B2.3), (A1.1)+(B2.4), (A1.2)+(B2.1), (A1.2)+(B2.2), (A1.2)+(B2.3), (A1.2)+(B2.4), (A1.1)+(B3.1), (A1.1)+(B3.2), (A1.1)+(B3.3), (A1.1)+(B3.4), (A1.1)+(B3.5), (A1.2)+(B3.1), (A1.2)+(B3.2), (A1.2)+(B3.3), (A1.2)+(B3.4), (A1.2)+(B3.5), (A1.1)+(B4.1), (A1.1)+(B4.2). (A1.1)+(B4.3), (A1.2)+(B4.1), (A1.2)+(B4.2), (A1.2)+(B4.3), (A2.2)+(B1.1), (A2.2)+(B1.2), (A2.2)+(B1.3), (A2.2)+(B1.4), (A2.2)+(B1.5), (A2.2)+(B1.6), (A.2.2)+(B1.7), (A2.2)+(B2.1), (A2.2)+(B2.2), (A2.2)+(B2.3), (A2.2)+(B2.4), (A2.2)+(B3.1), (A2.2)+(B3.2), (A2.2)+(B3.3), (A2.2)+(B3.4), (A2.2)+(B3.5), (A2.2)+(B4.1), (A2.2)+(B4.2), (A2.2)+(B4.3).

The combination of a compound (A) with one or more compounds (B0) is by definition a combination of two or more compounds from group (A). Since the herbicides (A) have a broad activity, such a combination requires that the transgenic plants or mutants show cross resistance to various herbicides (A). Such cross-resistances in transgenic plants have already been disclosed, cf. WO-A-98/20144.

In individual cases, it may be meaningful to combine one or more of the compounds (A) with a plurality of compounds (B), preferably from amongst the classes (B1), (B2), (B3) and (B4).

Furthermore, the combinations according to the invention can be employed together with other active ingredients, for example from the group of the safeners, fungicides, insecticides and plant growth regulators or from the group of the formulation aids and additives conventionally used in crop protection.

Examples of additives are fertilizers and colorants.

Preference is given to herbicide combinations of one or more compounds (A) with one or more compounds of group (B1) or (B2) or (B3) or (B4). Preference is furthermore given to combinations of one or more compounds (A), for example (A1.2)+(A2.2), preferably of one compound (A), and one or more compounds (B) following the scheme:

(A)+(B1)+(B2), (A)+(B1)+(B3), (A)+(B1)+(B4), (A)+(B2)+(B3), (A)+(B2)+(B4), (A)+(B3)+(B4), (A)+(B1)+(B2)+(B3), (A)+(B1)+(B2)+(B4), (A)+(B1)+(B3)+(B4), (A)+(B2)+(B3)+(B4).

Here, those combinations to which one or more further active ingredients with a different structure [active ingredient (C)], e.g. safeners or other herbicides, are additionally added, such as (A)+(B1)+(C), (A)+(B2)+(C), (A)+(B3)+(C) or (A)+(B4)+(C), (A)+(B1)+(B2)+(C), (A)+(B1)+(B3)+(C), (A)+(B1)+(B4)+(C), (A)+(B2)+(B4)+(C), or (A)+(B3)+(B4)+(C), are also in accordance with the invention.

The preferred conditions explained hereinbelow in particular for two-way combinations according to the invention primarily also apply to combinations of the last-mentioned type with three or more active ingredients, as long as they comprise the two-way combinations according to the invention, and with regard to the two-way combination according to the invention.

Also of particular interest is the use according to the invention of the combinations of one or more herbicides from group (A), preferably (A1.2) or (A2.2), in particular (A1.2), and one or more herbicides, preferably one herbicide, from the group (B1') metazachlor, trifluralin, clomazone, napropamide, carbetamide and dimefuron and/or, if appropriate, dimethachlor and/or (B2') quinmerac, clopyralid and ethametsulfuron-methyl and/or (B3') quizalofop-P/quizalofop and its esters, fenoxaprop-P/fenoxaprop and its esters, fluazifop-P/fluazipop and its esters, haloxyfop, haloxyfop-P and their esters, preferably fenoxaprop-P, fluazifop-P, haloxyfop, haloxyfop-P and their esters, and/or (B4') sethoxydim, cycloxydim and clethodim.

Preferred in this context are the combinations of the particular component (A) and one or more herbicides from group (B1'), (B2'), (B3') or (B4').

Furthermore preferred are the combinations (A)+(B1')+(B2'), (A)+(B1')+(B3'), (A)+(B1')+(B4'), (A)+(B2')+(B3'), (A)+(B2')+(B4') or (A)+(B3')+(B4').

Some of the combinations mentioned are new and as such also form part of the subject matter of the invention.

The combinations according to the invention (=herbicidal compositions) have an excellent herbicidal activity against a broad range of economically important monocotyledonous and dicotyledonous weeds. The active substances act equally well on perennial weeds which produce shoots from rhizomes, root stocks or other perennial organs and which cannot be easily controlled. In this context, it does not matter whether the substances are applied before sowing, pre-emergence or post-emergence. Preference is given to use post-emergence or early post-sowing pre-emergence.

Some representatives of the monocotyledonous and dicotyledonous weed flora which can be controlled by the compounds according to the invention may be mentioned individually as examples, but this is not to be taken to mean a restriction to certain species.

The monocotyledonous weed species which are controlled well are, for example, Avena spp., Setaria spp., Agropyron spp. and wild forms of cereals, but also Alopecurus spp., Digitaria spp., Lolium spp., Echinochloa spp., Phalaris spp., Poa spp., and Cyperus species from the annual group, and Cynodon, Imperata and Sorghum or else perennial Cyperus species amongst the perennial species.

In the case of dicotyledonous weed species, the spectrum of action extends to species such as, for example, chenopodium spp., Matricaria spp., Kochia spp., Veronica spp., Viola spp., Anthemis spp., Stellaria spp., Thlaspi spp., Galium spp., Datura spp., Cupsella spp. and Cirsium spp., but also Abutilon spp., Amaranthus spp., Chrystanthemum spp., Ipomoea spp., Lamium spp., Pharbitis spp., Sida spp. and Sinapis spp., Convolvulus, Rumex and Artemisia.

If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely.

When the active ingredients are applied post-emergence to the green parts of the plants, growth also stops drastically very soon after the treatment, and the weeds remain at the growth stage of the time of application, or, after a certain period of time, they die completely so that competition by the weeds, which is detrimental for the crop plants, is thus eliminated at a very early stage and in a sustained manner.

In comparison with the individual products, the herbicidal compositions according to the invention are distinguished by a herbicidal action which has a faster onset and is more prolonged. As a rule, the rainfastness of the active ingredients of the combinations according to the invention is advantageous. A particular advantage is that the dosages of compounds (A) and (B) which are used in the combinations and which are effective can be set at such a low level that their soil action is optimal. Thus, their use is not only made possible in the first place in sensitive crops, but groundwater combinations are virtually avoided. The combination according to the invention of active ingredients makes it possible to reduce the required application rate of the active ingredients considerably.

When herbicides of the type (A)+(B) are applied jointly, superadditive (=synergistic) effects are observed. Here, the action in the combinations exceeds the expected total of the actions of the individual herbicides employed. The synergistic effects permit a reduction in application rate, the control of a broader spectrum of broad-leaved and grass weeds, more rapid onset of the herbicidal action, a prolonged long-term action, better control of the harmful plants with only one, or few, applications, and a widening of the application period which is possible. In some cases, the use of the compositions also reduces the amount of harmful constituents in the crop plant, such as nitrogen or oleic acid.

The abovementioned properties and advantages are required in weed control practice to keep agricultural crops free of undesired competing plants and thus to guarantee the yields in qualitative and quantitative terms, and/or to increase the yields. These novel combinations far exceed the state of the art with regard to the properties described.

Although the compounds according to the invention have an outstanding herbicidal activity against monocotyledonous and dicotyledonous weeds, the tolerant, or cross-tolerant, oil-seed rape plants only suffer negligible damage, if any.

In addition, some of the compositions according to the invention have outstanding growth-regulatory properties in the oil-seed rape plants. They engage in the plants' metabolism in a regulatory manner and can therefore be employed for the targeted control of plant constituents. Moreover, they are also suitable for generally regulating and inhibiting undesired vegetative growth without killing the plants in the process. The inhibition of vegetative growth is very important in a large number of monocotyledonous and dicotyledonous crops since it can reduce, or completely prevent, lodging.

Owing to their herbicidal and plant-growth-regulatory properties, the compositions can be employed for controlling harmful plants in known tolerant or cross-tolerant oil-seed rape crops or in tolerant or genetically modified oil-seed rape crops which are yet to be developed. As a rule, the transgenic plants are distinguished by particularly advantageous properties, for example in addition to the resistances to the compositions according to the invention by resistances to fungal diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased oil content or whose quality has been modified, for example the fatty acid spectrum of the harvested material is different.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624).

For example, several cases of the following have been described:
  recombinant modifications of crop plants for the purposes of modifying the starch synthesized in the plants (for example WO 92/11376, WO 92/14827, WO 91/19806),
  transgenic crop plants which exhibit resistances to other herbicides, for example to sulfonylureas (EP-A-0257993, U.S. Pat. No. 5,013,659),
  transgenic crop plants with the ability of producing *Bacillus thuringiensis* toxins (*Bt* toxins), which make the plants resistant to certain pests (EP-A-0142924, EP-A-0193259),
  transgenic crop plants with a modified fatty acid spectrum (WO 91/13972).

A large number of techniques in molecular biology, with the aid of which novel transgenic plants with modified properties can be generated, are known in principle; see, for example, Sambrook et al., 1989, Molecular Cloning, A Laboratory Manual, $2^{nd}$ Ed., Cold Spring Harbor Laboratory Press, Cold Spring Harbor, N.Y.; or Winnacker "Gene und Klone" [Genes and Clones], VCH Weinheim $2^{nd}$ Edition 1996 or Christou, "Trends in Plant Science" 1 (1996) 423–431).

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves trans-scripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give intact plants. In principle, the transgenic plants can be plants of any desired plant species, i.e. both monocotyledonous and dicotyledonous plants.

Thus, transgenic plants can be obtained which exhibit modified properties owing to the overexpression, suppression or inhibition of homologous (=natural) genes or gene sequences or expressing heterologous (=foreign) genes or gene sequences.

A subject matter of the invention is therefore also a method of controlling undesired vegetation in tolerant oilseed rape crops, which comprises applying one or more herbicides of type (A) together with one or more herbicides of type (B) to the harmful plants, organs thereof or the area under cultivation.

Subject matter of the invention are also the novel combinations of compounds (A)+(B) and herbicidal compositions comprising them.

The active ingredient combinations according to the invention can both exist as mixed formulations of the two components, if appropriate together with further active ingredients, additives and/or customary formulation aids, which are then applied in the customary manner as a dilution with water, and be produced as so-called tank mixes by jointly diluting the separately formulated, or partially separately formulated, components with water.

The compounds (A) and (B) or their combinations can be formulated in various ways, depending on the prevailing biological and/or chemico-physical parameters. Examples of general formulation possibilities which are suitable are: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed-dressing materials, granules for soil application or spreading, or water-dispersible granules (WG), ULV formulations, microcapsules or waxes.

The individual formulation types are known in principle and are described, for example, in: Winnacker-Küchler, "Chemische Technologie" [Chemical Engineering], Volume 7, C. Hauser Verlag Munich, $4^{th}$ Ed. 1986; van Valkenburg, "Pesticides Formulations", Marcel Dekker N.Y., 1973; K. Martens, "Spray Drying Handbook", $3^{rd}$ Ed. 1979, G. Goodwin Ltd. London.

The necessary formulation aids, such as inert materials, surfactants, solvents and further additives, are also known and are described, for example, in: Watkins, "Handbook of Insecticide Dust Diluents and Carriers", $2^{nd}$ Ed., Darland Books, Caldwell N.J.; H.v. Olphen, "Introduction to Clay Colloid Chemistry"; $2^{nd}$ Ed., J. Wiley & Sons, N.Y. Marsden, "Solvents Guide", $2^{nd}$ Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesellschaft, Stuttgart 1976, Winnacker-Küchler, "Chemische Technologie", Volume 7, C. Hauser Verlag Munich, $4^{th}$ Ed. 1986.

Based on these formulations, it is also possible to prepare combinations with other pesticidally active substances, such as other herbicides, fungicides or insecticides, and with safeners, fertilizers and/or growth regulators, for example in the form of a ready mix or a tank mix.

Wettable powders (sprayable powders) are products which are uniformly dispersible in water and which, besides a diluent or inert material, additionally comprise ionic or nonionic surfactants (wetters, dispersants), for example polyethoxylated alkylphenols, polyethoxylated fatty alcohols or fatty amines, afkanesulfonates or alkylbenzenesulfonates, sodium lignosulfonate, sodium 2,2'-dinaphthylmethane-6,6-disulphonate, sodium dibutylnaphthalenesulfonate, or else sodium oleoylmethyltauride.

Emulsifiable concentrates are prepared by dissolving the active ingredient in an organic solvent, for example butanol, cyclohexanone, dimethylformamide, xylene, or else higher-boiling aromatics or hydrocarbons with addition of one or more ionic or nonionic surfactants (emulsifiers). Examples of emulsifiers which can be used are: calcium alkylarylsulfonates such as calcium dodecylbenzenesulfonate or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active ingredient with finely divided solid materials, for example talc, natural clays such as kaolin, bentonite and pyrophyllite, or diatomaceous earth.

Granules can be prepared either by spraying the active ingredient onto adsorptive, granulated inert material or by applying active ingredient concentrates by means of binders, for example polyvinyl alcohol, sodium polyacrylate or else mineral oils, to the surface of carriers such as sand, kaolinites or of granulated inert material. Also, suitable active ingredients may be granulated in the manner customary for the preparation of fertilizer granules, if desired as a mixture with fertilizers. Water-dispersible granules are, as a rule, prepared by methods such as spray drying, fluidized-bed granulation, disk granulation, mixing with high-speed mixers and extrusion without solid inert material.

As a rule, the agrochemical preparations comprise 0.1 to 99 percent by weight, in particular 2 to 95% by weight, of active ingredients of types A and/or B, the following concentration being customary, depending on the formulation type:

In wettable powders, the active ingredient concentration is, for example, approximately 10 to 95% by weight, the remainder to 100% being composed of customary formulation components. In the case of emulsifiable concentrates, the active ingredient concentration can amount to, for example, 5 to 80% by weight.

Formulations in the form of dusts usually comprise 5 to 20% by weight of active ingredient, sprayable solutions approximately 0.2 to 25% by weight of active ingredient.

In the case of granules, such as dispersible granules, the active ingredient content depends partly on whether the active ingredient is in liquid or solid form and on which granulation auxiliaries and fillers are being used. As a rule, the content in the case of the water-dispersible granules ranges between 10 and 90% by weight.

In addition, the abovementioned active ingredient formulations comprise, if appropriate, the binders, wetters, dispersants, emulsifiers, preservatives, antifreeze agents, solvents, fillers, colorants, carriers, antifoams, evaporation inhibitors, pH regulators or viscosity regulators which are conventional in each case.

For example, it is known to improve the action of glufosinate-ammonium (A1.2) and that of its L-enantiomer by surface-active substances, preferably by wetters from the series of the alkyl polyglycol ether sulfates which contain, for example, 10 to 18 carbon atoms and which are used in the form of their alkali metal or ammonium salts, but also as the magnesium salt, such as sodium $C_{12}/C_{14}$ fatty alcohol diglycol ether sulfate (®Genapol LRO, Hoechst); see EP-A-0476555, EP-A-0048436, EP-A-0336151 or U.S. Pat. No. 4,400,196 and Proc. EWRS Symp. "Factors Affecting Herbicidal Activity and Selectivity", 227–232 (1988). Furthermore, it is known that alkyl polyglycol ether sulfates are also suitable as penetrants and synergists for a series of other herbicides, inter alia also herbicides from the series of the imidazolinones; see EP-A-0502014.

For use, the formulations, which are present in commercially available form, are, if appropriate, diluted in the customary manner, for example using water in the case of wettable powders, emulsifiable concentrates, dispersions and water-dispersible granules. Preparations in the form of dusts, soil granules, granules for spreading and sprayable solutions are usually not diluted further with other inert materials prior to use.

The active ingredients can be applied to the plants, plant organs, plant seeds or the area under cultivation (soil of a field), preferably to the green plants and plant organs and, if appropriate, additionally to the soil of the field.

One possibility of using the active ingredients is their joint application in the form of tank mixes, where the optimally formulated concentrated formulations of the individual active ingredients are mixed jointly in the tank with water, and the resulting spray mixture is applied.

A joint herbicidal formulation of the combination according to the invention of (A) and (B) has the advantage that it is easier to apply since the amounts of the components are preset in the correct ratio to each other. Also, the auxiliaries in the formulation can be matched optimally to each other, while a tank mix of different formulations may lead to undesired combinations of auxiliaries.

A. GENERAL FORMULATION EXAMPLES a) A dust is obtained by mixing 10 parts by weight of an active ingredient/active ingredient mixture and 90 parts by weight of talc as inert substance and comminuting the mixture in a hammer mill, b) A wettable powder which is readily dispersible in water is obtained by mixing 25 parts by weight of an active ingredient/active ingredient mixture, 64 parts by weight of kaolin-containing quartz as inert substance, 10 parts by weight of potassium lignosulfonate and 1 part by weight of sodium oleoylmethyltauride as wetter and dispersant and grinding the mixture in a pinned-disc mill.

c) A dispersion concentrate which is readily dispersible in water is obtained by mixing 20 parts by weight of an active ingredient/active ingredient mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to 277° C.) and grinding the mixture in a bowl mill to a fineness of below 5 microns.

d) An emulsifiable concentrate is obtained from 15 parts by weight of an active ingredient/active ingredient mixture, 75 parts by weight of cyclohexanone as solvent and 10 parts by weight of oxethylated nonylphenol as emulsifier.

e) Granules which are dispersible in water are obtained by mixing
   75 parts by weight of an active ingredient/active ingredient mixture,
   10 parts by weight of calcium lignosulfonate,
   5 parts by weight of sodium lauryl sulfate,
   3 parts by weight of polyvinyl alcohol and
   7 parts by weight of kaolin,
   grinding the mixture in a pinned-disc mill and granulating the powder in a fluidized bed by spraying on water as granulation liquid.

f) Water-dispersible granules are also obtained by homogenizing and precomminuting, on a colloid mill,
   25 parts by weight of an active ingredient/active ingredient mixture,
   5 parts by weight of sodium 2,2'-dinaphthylmethane-6,6'-disulfonate,
   2 parts by weight of sodium oleoylmethyltauride,
   1 part by weight of polyvinyl alcohol,
   17 parts by weight of calcium carbonate and
   50 parts by weight of water,
   subsequently grinding the mixture in a bead mill and atomizing and drying the resulting suspension in a spray tower by means of a single-substance nozzle.

B. BIOLOGICAL EXAMPLES

1. Pre-emergence Action on Weeds

Seeds or rhizome pieces of monocotyledonous and dicotyledonous harmful plants are placed in sandy loam in cardboard pots and covered with soil. The compositions, which are formulated in the form of concentrated aqueous solutions, wettable powders or emulsion concentrates, are then applied to the surface of the covering soil at various dosages as aqueous solution, suspension or emulsion at an application rate of 600 to 800 l of water per ha (converted). After the treatment, the pots are placed in the greenhouse and kept under good growth conditions for the weeds. Visual scoring of the plant damage or the adverse effect on emergence was done after the test plants had emerged after an experimental period of 3 to 4 weeks in comparison with untreated controls. As shown by the test results, the compositions according to the invention have a good herbicidal pre-emergence activity against a broad spectrum of grass weeds and broad-leaved weeds.

In this context, activities of the combinations according to the invention are frequently observed which exceed the formal total of the activities when the herbicides are applied individually (=synergistic effect).

If already the observed activity values exceed the formal total (=$E^A$) of the values in the experiments with individual application, then they also exceed Colby's expected value (=$E^c$), which is calculated by the following formula and which is also regarded as indicating synergism (cf. S. R. Colby; in Weeds 15 (1967) pp. 20 to 22):

$$E^c = A + B - (A \cdot B/100)$$

In this formula, A, B indicate the activity of the active ingredients A and B in % at a and b g A.S./ha, respectively, and $E^c$ indicates the expected value in % at a+b g A.S./ha.

At suitable low dosages, the observed experimental values show an effect of the combinations which exceeds Colby's expected values.

2. Post-emergence Action on Weeds

Seeds or rhizomes of monocotyledonous and dicotyledonous weeds are placed in sandy loam soil in cardboard pots, covered with soil and grown in the greenhouse under good growth conditions. Three weeks after sowing, the experimental plants are treated at the three-leaf stage with the compositions according to the invention. The compositions according to the invention, which are formulated as wettable powders or as emulsion concentrates, are sprayed at various dosages onto the green plant organs at an application rate of 600 to 800 l of water per ha (converted). After the experimental plants have remained in the greenhouse for approx. 3 to 4 weeks under optimal growth conditions, the effect of the preparations is scored visually in comparison with untreated controls. The compositions according to the invention also have a good herbicidal activity against a broad spectrum of economically important grass weeds and broad-leaved weeds when applied post-emergence.

In this context, activities of the combinations according to the invention are frequently observed which exceed the formal total of the activities when the herbicides are applied individually. The observed values show, at suitably low dosages, an activity of the combinations which exceed Colby's expected values (cf. scoring in Example 1).

3. Herbicidal Action and Crop Plant Tolerance (Field Trial)

Transgenic oil-seed rape plants with resistance to one or more herbicides (A) were grown together with typical weed plants in the open in 2×5 m plots under natural field conditions; alternatively, the weed population established naturally while the oil-seed rape plants grew. Treatment with the compositions according to the invention and, for control purposes, with separate application of the active ingredients of the components alone, was carried out under standard conditions with a plot sprayer at an application rate of 200–300 liters of water per hectare in parallel trials in accordance with the scheme of Table 1, i.e. pre-sowing/pre-emergence, post-sowing/-pre-emergence or post-emergence at the early, medium or late stage.

TABLE 1

Use scheme - Examples

| Application of the active ingredients | Pre-emergence | Post-emergence after sowing | Post-emergence up to the 2-leaf stage | Post-emergence 2–4-leaf stage | Post-emergence 6-leaf stage |
|---|---|---|---|---|---|
| combined | (A) + (B) | | | | |
| " | | (A) + (B) | | | |
| " | | | (A) + (B) | | |
| " | | | | (A) + (B) | |
| " | | | | | (A) + (B) |
| sequential | (A) | | (B) | | |
| " | | (A) | (B) | | |
| " | | (A) | | (B) | |
| " | | (A) | (A) | (B) | |
| " | | (A) | | (B) | (B) |
| " | | (A) | | (A) + (B) | |
| " | (B) | | (A) | | |
| " | | (B) | | (A) + (B) | |
| " | (A) + (B) | | (A) + (B) | | |
| " | (A) + (B) | (A) + (B) | (A) + (B) | | |
| " | | (A) + (B) | (A) + (B) | | |
| sequential | | (A) + (B) | (A) + (B) | (A) + (B) | |
| " | | (A) + (B) | (A) + (B) | (A) + (B) | (A) + (B) |
| " | | | (A) + (B) | (A) + (B) | |
| " | | | (A) + (B) | (A) + (B) | (A) + (B) |
| " | | | | (A) + (B) | (A) + (B) |

At 2, 4, 6 and 8 week intervals after application, the herbicidal activity of the active ingredients or active ingredient mixtures were scored visually by comparing the treated plots with untreated control plots. Damage and development of all aerial plant organs was recorded. The scoring was done using a percentage scale (100% activity= all plants dead; 50% activity=50% of the plants and green plant organs dead; 0% activity=no discernible effect=like control plot). The score values of in each case 4 plots were averaged.

The comparison demonstrated that the combinations according to the invention usually exhibit a greater, in some cases considerably greater, herbicidal activity than the total of the actions of the individual herbicides. In important sections of the score period, the activities exceeded Colby's expected values (cf. score in Example 1) and therefore suggest that synergism is present. In contrast, the oil-seed rape plants suffered no, or only negligible, damage as a consequence of the treatment with the herbicidal compositions.

Abbreviations used in the tables in general form:

| | |
|---|---|
| g of A.S./ha = | grams of active substance (100% active ingredient) per hectare |
| $E^A$ = | total of the herbicidal actions of the individual applications |
| $E^C$ = | expected value according to Colby (cf. score in table 1) |
| "Oil-seed rape LL" = | ® Liberty-Link oil-seed rape which is resistant or tolerant to glufosinate-ammonium, |

TABLE 2

Herbicidal action in the oil-seed rape field trial

| Active ingredient(s) | Dose[1] g of A.S./ha | Herbicidal action[2] (%) against Datura stramonium |
|---|---|---|
| (A1.2) | 600 | 90 |
| (B1.1) | 600 | 40 |
|  | 1200 | 93 |
| (A1.2) + (B1.1) | 600 + 600 | 100 ($E^C$ = 94) |

Abbreviations for table 2:
[1] = application in the 5-leaf stage
[2] = scoring 3 weeks after application
(A1.2) = glufosinate-ammonium
(B1.1) = metazachlor

TABLE 3

Herbicidal action in oil-seed rape field trial

| Active ingredient(s) | Dose[1] g of A.S./ha | Herbicidal action[2] (%) against Galium aparine | Oil-seed rape LL |
|---|---|---|---|
| (A1.2) | 500 | 63 | 3 |
|  | 250 | 41 | 0 |
|  | 125 | 15 | 0 |
| (B1.5) + (B1.6) | 1500 + 750 | 73 | 5 |
|  | 750 + 375 | 45 | 4 |
| (A1.2) + (B1.5) + (B1.6) | 125 + (750 + 375) | 78 ($E^A$ = 15 + 45) | 3 |
|  | 250 (750 + 375) | 88 ($E^A$ = 41 + 45) | 3 |

Abbreviations for table 3:
[1] = application in the 4–5 leaf stage
[2] = scoring 36 days after application
(A1.2) = glufosinate-ammonium
(B.15) = carbetamide
(B1.6) = dimefuron

TABLE 4

Herbicidal action in the field trial

| Active ingredient(s) | Dose[1] g of A.S./ha | Herbicidal action[2] % against Matricaria chamomita |
|---|---|---|
| post-emergence application: | 500 | 65 |
| (A1.2) | 250 | 35 |
|  | 125 | 10 |
| pre-sowing application: (B1.2) + (B1.4) | 950 + 1200 | 45 |
| Sequence: pre-sowing application of [(B1.4) + (B1.3)] followed by post-emergence application of (A1.2) | (950 + 1200) + 250 | 80 ($E^C$ = 64.3) |
| post-emergence application: (B1.1) + (B2.1) | 600 + 200 | 83 |
| post-emergence application: (A1.2) + (B1.1) + (B2.1) | 125 + 600 + 200 | 95 ($E^A$ = 93) |
| post-emergence (B2.1) | 300 | 50 |
| (A1.2) + (B2.1) | 125 + 300 | 65 ($E^A$ = 60) |
| post-emergence (B2.3) | 600 | 60 |
| (A1.2) + (B2.3) | 125 + 600 | 75 ($E^A$ = 70) |

Abbreviations for table 4:
[1] = post-emergence application in the 4-leaf stage or pre-emergence application, as stated
[2] = scoring in each case 35 days after pre-sowing application and 28 days after post-emergence application
(A1.2) = glufosinate-ammonium
(B1.4) = napromide

TABLE 4-continued

Herbicidal action in the field trial (B1.2) = trifluralin
(B1.1) = metazachlor
(B2.1) = quinmerac
(B2.3) = pyridate

TABLE 5

Herbicidal action in field trial

| Active ingredient(s) | Dose[1] g of A.S./ha | Herbicidal action[2] (%) against Cirsium arvense | Chenopodium album | Oil-seed rape LL |
|---|---|---|---|---|
| (A1.2) | 350 | 97 | — | 0 |
|  | 230 | 85 | 90 | 0 |
| (B2.4) | 15 | 0 | 30 | 0 |
| (A1.2) + (B2.4) | 230 + 15 | 98 ($E^A$ = 85) | 100 ($E^C$ = 93) | 0 |
| (B2.2) | 90 | 85 | 50 | 0 |
| (A1.2) + (B2.2) | 230 + 90 | 100 ($E^C$ = 98) | 85 ($E^A$ = 80) | 0 |

Abbreviations for table 5:
[1] = application in the 4-leaf stage
[2] = scoring 15 days after application
(A1.2) = glufosinate-ammonium
(B2.2) = clopyralid
(B2.4) = ethametsulfuron-methyl

What is claimed is:
1. A herbicidal composition which comprises a combination comprising
A) at least one broad-spectrum herbicide selected from the group consisting of
A1) compounds of the formula (A1)

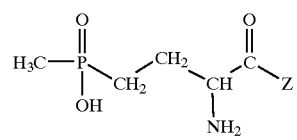

(A1)

in which Z is a radical of the formula —OH or a peptide residue of the formula —NHCH(CH$_3$)CONHCH(CH$_3$)COOH or —NHCH(CH$_3$)CONHCH[CH$_2$CH(CH$_3$)$_2$]COOH, or its esters or salts, or other phosphinothricin derivatives,
A2) compounds of the formula (A2) or their esters and salts,

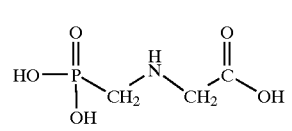

(A2)

A3) imidazolinones or their salts; and
A4) herbicidal azoles, which are inhibitors of protoporphrinogen oxidase (PPO inhibitors)
B) at least one herbicidal compound selected from the group consisting of
B1') metazachlor, clomazone, napropamide, carbetamide, dimefuron and dimethachlor,
B2') quinmerac, clopyralid and ethametsulfuron-methyl or B3') fenoxaprop-P or its esters, fluazifop-P or its esters, haloxyfop or its esters, haloxyfop-P or its esters, and B4') sethoxydim, cycloxydim or clethodim and, optionally, at least one additive, and/or formulation aid conventionally used in crop protection with the exception of herbicidal compositions wherein compound (A2) in combination with fluazifop-P, sethoxydim or clethodim.

2. A herbicidal composition which consists essentially of
A) at least one broad-spectrum herbicide selected from the group consisting of
A1) compounds of the formula (A1)

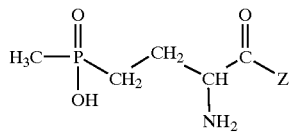

(A1)

in which Z is a radical of the formula —OH or a peptide residue of the formula —NHCH(CH₃)CONHCH(CH₃)COOH or —NHCH(CH₃)CONHCH[CH₂CH(CH₃)₂]COOH, or its esters or salts, or other phosphinothricin derivatives, A3) imidazolinones or their salts; and A4) herbicidal azoles which are inhibitors or protoporphrinogen oxidase (PPO inhibitors)

B) at least one herbicide compound selected from the group consisting of

B1') metazachlor, clomazone, napropamide, carbetamide, dimefuron and dimethachlor or B2') quinmerac, clopyralid and ethametsulfuron-methyl or B3') fenoxaprop-P and its esters, fluazifop-P or its esters, haloxyfop or its esters, haloxyfop-P or its esters and B4') sethoxydim, cycloxydim or clethodim and, optionally, additives and/or formulation aids conventionally used in crop protection.

3. Herbicidal composition which comprises glufosinate-ammonium in combination with one or more herbicides from the group (B1') metazachlor, trifluralin, clomazone, napropamide, carbetamide, dimefuron and dimethachlor or (B2') quinmerac, clopyralid and ethametsulfuron-methyl or (B3') fenoxaprop-P and its esters, fluazifop-P and its esters, haloxyfop, haloxyfop-P and their esters or (B4') sethoxydim, cycloxydim and clethodim or a combination of more than one herbicide of the groups (B1') to (B4') and, if appropriate, formulation aids and additives conventionally used in crop protection.

4. A herbicidal composition which comprises glufosinate-ammonium in combination with at least one herbicide selected from the group consisting of B1') metazachlor, trifluralin, clomazone, napropamide, carbetamide, dimefuron or dimethachlor, B2') quinmerac, clopyralid and ethametsulfuron-methyl or, B3') fenoxaprop-P or its ester, fluazifop-P or its ester, haloxyfop, haloxyfop or its ester haloxyfop-P or its ester or, B4') sethoxydim, cycloxydim or clethodim and optionally at least one formulation aid and/or additive conventionally used in crop protection.

5. A method for controlling harmful plants in oil-seed rape crops, which comprises applying to the crops, seeds, plants, plant organs, or area under cultivation a synergistically effective amount of a combination of A) at least one broad-spectrum herbicide selected from the group consisting of A1) compounds of the formula (A1)

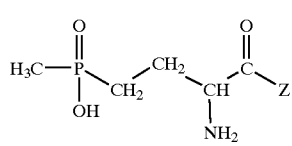

(A1)

in which Z is a radical of the formula —OH or a peptide residue of the formula —NHCH(CH₃)CONHCH(CH₃)COOH or —NHCH(CH₃)CONHCH[CH₂CH(CH₃)₂]COOH, or its esters or salts, or other phosphinothricin derivatives, A2) compounds of the formula (A2) or their esters or salts,

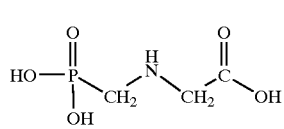

(A2)

A3) imidazolinones or their salts and

A4) herbicidal azoles salts, which are protoporphrinogen oxidase (PPO inhibitors) and B) at least one herbicidal compound selected from the group consisting of B0) herbicides (A) from the group of the herbicides (A1) to (A4), which are not identical to that of component (A), B1) metazachlor, trifluralin, clomazone, napropamide, carbetamide, dimefuron or dimethachlor, B2) quinmerac, clopyralid, pyridate or ethametsulfuron-methyl, B3) quizalofop-P or its esters, fenoxaprop-P or its esters, fluazifop-P or its esters, haloxyfop or haloxyfop-P or its esters or propaquizafop; and B4) sethoxydim, cycloxydim or clethodim, and optionally safeners whereby the oil-seed rape crops tolerate the broad spectrum herbicides (A) and the herbicidal compounds (B)

with the exception of herbicide combinations wherein
a) compound (A1) is in combination with the compound propaquizafop,
b) compound (A2) is in combination with the compound propaquizafop or trifluralin.

6. The method as claimed in claim 5, wherein the broad spectrum herbicide is glufosinate-ammonium.

7. The method as claimed in claim 6, wherein the herbicidal compound (B) are selected from the group consisting of B1) metazachlor, trifluralin, clomazone, napropamidem carbetamide, dimefuron or dimethachlor B2) quinmerac, clopyralid, pyridate or ethametsulfuron-methyl, B3) quizalofop-P or its esters, fenoxaprop-P or its esters, fluazifop-P or its esters, haloxyfop or its esters or haloxyfop-P or its esters; and B4) sethoxydim, cycloxydim or clethodim.

8. The method as claimed in claim 5, wherein the broad spectrum herbicide is glyphosate-isopropyl-ammonium.

9. The method as claimed in claim 5, wherein herbicidal compounds (B) are selected from the group consisting of
B0) herbicides (A) from the group of herbicides (A1) to (A4) which are not identical to that of component (A),
B1) metazachlor, clomazone, napropamide, carbetamide, dimefuron or dimethachlor,
B2) quinmerac, clopyralid, pyridate or ethametsulfuron-methyl,
B3) quizalofop-P or its esters, fenoxaprop-P or its esters, fluazifop-P or its esters, haloxyfop, or its esters, and haloxyfop-P or its esters; and
B4) sethoxydim, cycloxydim or clethodim.

10. The method as claimed in claim 5, wherein the combination further comprises additional active ingredients used in crop protection.

11. The method as claimed in claim 5, wherein the combination is applied jointly with auxiliaries conventionally used in crop protection and/or formulation aids.

12. The method according to claim 5, wherein the PPO inhibitors is WC9717.

13. The method according to claim 5, wherein the broad spectrum herbicide is glyphosate or an alkali metal or amine salt thereof.

14. The method according to claim 5, wherein the combination is applied pre-emergently and the compounds comprising the combination are applied jointly or separately.

15. The method according to claim 5, wherein the combination is applied post-emergently and the compounds comprising the combination are applied jointly or separately.

16. The method according to claim 5, wherein the combination is applied both pre- and post-emergently.

17. A method for controlling harmful plants in oil-seed rape crops, which comprises applying to the crops, seeds, plants, plant organs or area under cultivation, a synergistic effective amount of a combination of
A) at least one broad-spectrum herbicide selected from the group consisting of
A1) compounds of the formula (A1)

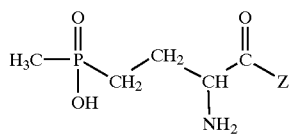

(A1)

in which Z is a radical of the formula —OH or a peptide residue of the formula —NHCH(CH$_3$)CONHCH(CH$_3$)COOH or —NHCH(CH$_3$)CONHCH[CH$_2$CH(CH$_3$)$_2$]COOH, or its esters or salts, or other phosphinothricin derivatives,
A3) imidazolinones or their salts; and
A4) herbicidal azoles which are protoporphrinogen oxidase (PPO inhibitors) and
B) at least one herbicide selected from the group consisting of
B0) herbicides (A) from the group of the herbicides (A1) (A3) or (A4), which are not identical to that of component (A),
B1) metazachlor, trifluralin, clomazone, napropamide, carbetamide, dimefuron or dimethachlor,
B2) quinmerac, clopyralid, pyridate, or ethametsulfuron-methyl,
B3) quizalofop-P or its esters, fenoxaprop-P or its esters, fluazifop-P or its esters, haloxyfop or its esters, haloxyfop-P or its esters, or propaquizafop; and
B4) sethoxydim, cycloxydim or clethodim and, optionally, one or more appropriate safeners,
whereby the oil-seed rape crops tolerate the herbicides (A) and (B) which are present in the combination with the exception of
herbicide combinations
a) compound (A1) in combination with the compound propaquizafop.

18. The method as claimed in claim 17, wherein the broad-spectrum herbicide is glufosinate-ammonium.

19. The method as claimed in claim 8, wherein the herbicidal compounds (B) are selected from the group consisting of
B1) metazachlor, trifluralin, clomazone, napropamidem carbetamide, dimefuron or dimethachlor,
B2) quinmerac, clopyralid, pyridate or ethametsulfuron-methyl,
B3) quizalofop-P or its esters, fenoxaprop-P or its esters, fluazifop-P or its esters, haloxyfop or its esters, and haloxyfop-P or its esters and
B4) sethoxydim, cycloxydim or clethodim.

20. The method as claimed in claim 17, wherein the herbicide compounds (B) are selected from the group consisting of
B0) herbicides (A) from the group of herbicides (A1), (A3), or (A4) which are not identical to that of component (A),
B1) metazachlor, clomazone, napropamide, carbetamide, dimefuron or dimethachlor,
B2) quinmerac, clopyralid, pyridate or ethametsulfuron-methyl,
B3) quizalofop-P or its esters, fenoxaprop-P or its esters, fluazifop-P or its esters, haloxyfop or its esters, or haloxyfop-P or its esters; and
B4) sethoxydim, cycloxydim or clethodim.

21. The method as claimed in claim 17, wherein the combination further comprises an additional active ingredient used in crop protection.

22. The method as claimed in claim 17, wherein the combination is used jointly with auxiliaries conventionally used in crop protection or formulation aids.

23. The method according to claim 17, wherein the combination is applied pre-emergently and the components are applied jointly or separately.

24. The method according to claim 17, wherein the combination is applied post-emergently and the compounds comprising the combination are applied jointly or separately.

25. The method according to claim 17, wherein the combination is applied both pre- and post-emergently.

* * * * *